Figure 1:
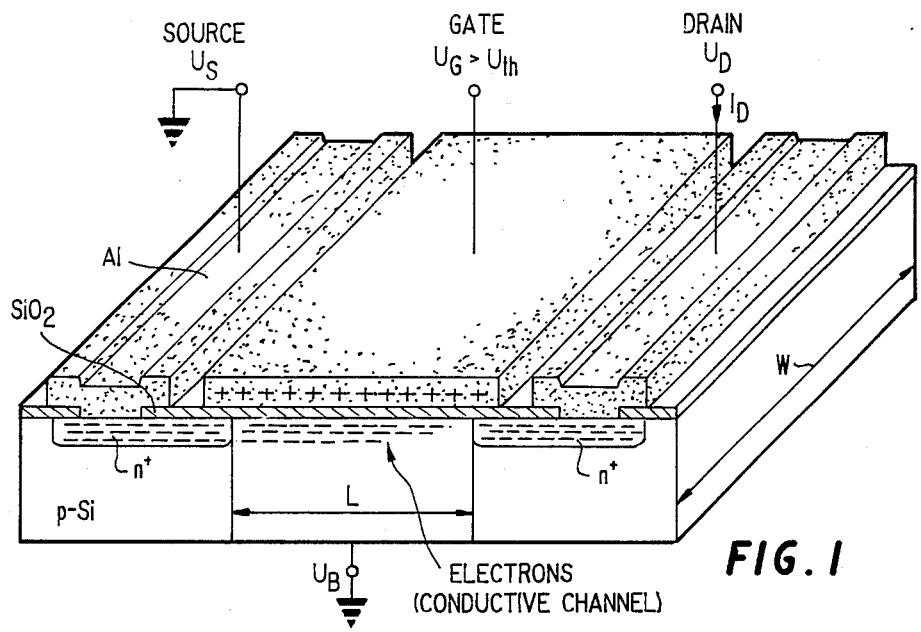

United States Patent [19]

Schmidt et al.

[11] Patent Number: 4,878,015
[45] Date of Patent: Oct. 31, 1989

[54] SENSORS FOR SELECTIVELY DETERMINING LIQUID-PHASE OR GAS-PHASE COMPONENTS USING A HETEROPOLYSILOXANE SENSITIVE LAYER

[75] Inventors: Helmut Schmidt, Zellingen; Frank Hutter, Würzburg; Karl-Heinz Haas, Theilheim; Ernst Obermeier, Kaufbeuren; Ulrich Steger, Munich; Hanns-Erik Endres, Munich; Stephan Drost, Munich, all of Fed. Rep. of Germany

[73] Assignee: Fraunhofer-Gesellschaft zur Forderung der angewandten Forschung e.V., Munich, Fed. Rep. of Germany

[21] Appl. No.: 44,506

[22] PCT Filed: Jul. 23, 1986

[86] PCT No.: PCT/EP86/00436
§ 371 Date: Mar. 23, 1987
§ 102(e) Date: Mar. 23, 1987

[87] PCT Pub. No.: WO87/00633
PCT Pub. Date: Jan. 29, 1987

[30] Foreign Application Priority Data

Jul. 23, 1985 [DE] Fed. Rep. of Germany ....... 3526348

[51] Int. Cl.⁴ ............................................. G01N 27/00
[52] U.S. Cl. .................................... 324/71.5; 204/418
[58] Field of Search ................. 324/71.5, 71.1; 357/23, 357/19, 29; 204/418, 419, 406, 435

[56] References Cited

U.S. PATENT DOCUMENTS 3,337,497  8/1967  Bostick .............................. 260/46.5
3,400,145 12/1965  G. E. ................................... 556/452
4,241,019 12/1980  Nakatani et al. .............. 324/71.5 X
4,269,682  5/1981  Yano et al. .......................... 204/418

FOREIGN PATENT DOCUMENTS 316144  9/1973  United Kingdom .
017400  3/1979  United Kingdom .

OTHER PUBLICATIONS

Journal of Applied Physics, vol. 51, No. 9, Sep. 1980 (US) M. Aktik et al.: "A New Polymer Insulated Gate Field-effect Transistor", pp. 5055–5057, see the whole article Primary Examiner—Reinhard J. Eisenzopf
Assistant Examiner—Jack B. Harvey
Attorney, Agent, or Firm—Oblon, Spivak, McClelland, Maier & Neustadt

[57] ABSTRACT

A description is given of sensors in in the form of field effect transistors and capacitors which are suitable for qualitatively and quantitatively determining species to be analyzed, for example molecules or ions, in liquid or gaseous media. A special field of application is the selective determination of the presence and concentration of gases. The sensors are defined in that they have a sensitive layer consisting of a heteropolysiloxane.

26 Claims, 11 Drawing Sheets

SENSORS FOR SELECTIVELY DETERMINING LIQUID-PHASE OR GAS-PHASE COMPONENTS USING A HETEROPOLYSILOXANE SENSITIVE LAYER

The invention relates to sensors for selectively determining liquid-phase or gas-phase components; in particular, the invention relates to field effect transistors and capacitors for qualitatively or quantitatively determining species to be analyzed (molecules, ions etc.) in liquids or gases.

In a MOS field effect transistor (Metal Oxide Semiconductor Field Effect Transistor; MOSFET), an embodiment of which is shown diagrammatically in FIG. 1, the gate electrode (e.g. aluminum) is separated from the semiconductor (e.g. silicon) by a single-layer or multi-layer gate insulator (e.g. silicon dioxide.) The voltage $U_G$ on the gate controls the current flow between drain and source electrode.

A distinction is made between n-channel and p-channel transistors:

In n-channel transistors electrons flow from the source region into the drain region. The drain electrode is at a higher potential than the source electrode.

In p-channel transistors "holes" flow from the source region into the drain region. The source electrode is at a higher potential than the drain electrode.

The transistors are furthermore divided into depletion and enhancement types:

Transistors of the depletion type (also termed depletion transistors) conduct even with a gate voltage of 0 V.

Transistors of the enhancement type (also described as hancement transistors) have no current flow at a gate voltage of 0 V.

Two operating conditions (a) blocking and (b) conducting are discussed below using an n-channel FET as the example and making reference to FIG. 2:

(a) The voltage $U_G$ on the gate electrode is less than the threshold voltage $U_{th}$: $U_G < U_{th}$. The source and drain regions (n-type silicon) have electrons as mobile majority carriers and the semiconductor in between (p-type silicon) has holes as mobile majority carriers. Since one of the two pn-junctions is always reverse biased, no current flows in this operating condition.

(b) The gate voltage is larger than the threshold voltage: $U_G > U_{th}$ The gate is positively charged to such an extent that an inversion layer consisting of electrons is produced at the semiconductor/insulator boundary layer. A channel has consequently formed underneath the gate so that electrons can now travel from the source region through this channel beneath the gate electrode to the drain. The more positive the gate voltage is, the more electrodes there are in the channel and the greater is the current flow.

The simplest formulae for an n-channel FET (current flow from $U_G > U_{th}$ upwards) are as follows, it being necessary to distinguish between the triode region and the saturation region (see FIG. 3): triode region:

$$U_D < U_{D\,sat} = U_G - U_{th} \quad (1)$$

$$I_D = \frac{\mu W \epsilon_{is}}{L d_{is}} \left( U_G - U_{th} - \frac{U_D}{2} \right) U_D$$

Saturation region:

$$U_D > U_{D\,sat} = U_G - U_{th}$$

$$I_D = \frac{\mu W \epsilon_{is}}{L d_{is}} \frac{(U_G - U_{th})^2}{2} \quad (2)$$

The drain current $I_D$ therefore depends on the following parameters:

$\mu$: Mobility of charge carriers in channel The greater the mobility is, the higher the current. Since electrons have a greater mobility than holes, an n-channel MOSFET conducts more current than a p-channel MOSFET for otherwise equal parameters.

W: Channel width The greater the width of the channel is, the greater is the current flow.

L: Length of channel The smaller L is, i.e. the smaller the distance between source region and drain region is, the greater the electrical field is between drain and source for a given voltage $U_D$ and the greater the current. For a high current, therefore, the ratio W/L must be large.

$C_{is}$: Insulator capacity per unit area: $C_{is} = \epsilon_{is}/d_{is}$ (3)

$\epsilon_{is}$: Dielectric constant of the gate insulator $d_{is}$: Thickness of the gate insulator Decreasing the insulator thickness produces a higher insulator capacitance so that, for the same gate voltage, there is a greater charge in the channel, i.e. a greater current flows. On the other hand, the insulator capacitance is proportional to the dielectric constant of the gate insulator so that if silicon nitride is used as insulator instead of silicon dioxide, a higher current is established.

$U_G$: Gate voltage The current increases as the gate voltage rises.

$U_{th}$: Threshold voltage For $U_G > U_{th}$, a current flows in an n-channel FET.

$U_D$: Drain voltage The current increases with rising drain voltage, but reaches a saturation value for $D_D > U_D$ sat.

The threshold value $U_{th}$ is made up of the following components:

$$U_{th} = \phi_m - \phi_{si} - \frac{Q_{is}}{C_{is}} - \frac{Q_b}{C_{is}} + 2\phi_p \quad (4)$$

$O_m$-$O_{si}$: Difference in the work functions of the metal (gate electrode) and silicon $Q_{is}$: Charge in gate insulator per unit area Depending on the manufacturing process, the silicon dioxide contains positive charges. The more positive charges there are in the oxide, the fewer the positive charges which have to be supplied to the gate for a certain current to flow; $U_{th}$ is consequently lower.

$Q_b$: Charge of the ionized dopant atoms in the depletion zone per unit area The magnitude of $Q_b$ depends on the doping of the silicon and the voltage $U_B$ on the substrate connection.

$$Q_b = -\sqrt{2\,\epsilon_{si}\,N_A\,e(2\phi_p - U_B)} \quad (5)$$

$\epsilon_{si}$: Dielectric constant of silicon
$N_A$: Density of dopant atoms (acceptors)
e: Elementary charge $2\phi_p$: Band bending in silicon which is necessary to produce an inversion layer.

$$2\phi_p = 2\frac{kT}{e} \ln(N_A/n_i) \quad (6)$$

k: Boltzmann constant
T: absolute temperature
$n_i$: charge carrier density for intrinsic conduction The gate voltage at which no band bending and consequently no space charge zone ($Q_b=0$) exist is termed the flat band voltage $U_{fb}$.

$$U_{fb} = \phi_m - \phi_{si} - \frac{Q_{is}}{C_{is}} \quad (7)$$

In the equations for the drain current and the threshold voltage there are a few parameters which cannot be influenced by the species to be analyzed (e.g. gases, or ions which are contained in a liquid). These are the semiconductor parameters such as the mobility $\mu$, the work function of the semiconductor $O_{Si}$ and the dopant (and consequently $Q_b$ and $20_p$), and also the geometrical dimensions W and L.

On the other hand in the case of the following parameters it is theoretically conceivable that they may be used to determine the presence and concentrations of a species to be analyzed:

Insulation capacitance $C_{is}=\epsilon_{is}/d_{is}$ (here a change in the dielectric constant $\epsilon_{is}$ is to the fore)

Work function $O_m$ of the metal or of another electrically conducting gate electrode Insulator charge $Q_{is}$ As is evident from equation 4, a change in $O_m$ or $Q_{is}$ has an effect on the threshold voltage $U_{th}$. A change in $\epsilon_{is}$ affects the drain current $I_D$ both directly (equations 1 and 2) and also indirectly via the threshold voltage (equation 4).

In practice, the sensors differ according to the working medium (gaseous or liquid). The ISFET (Ion-Sensitive Field Effect Transistor) shown in FIG. 4, for example, is used for measurement in liquids. Measurable parameters are, for example, the pH ($Si_3N_4$ gate insulator) and the concentration of ions such as $Na^+$, $K^+$ or $Ca^{++}$ (ion-sensitive layer in addition above the gate insulator). The ISFET operates on the following principle: a potential difference is established at the boundary between solution and gate insulator or ion-sensitive layer depending on the pH or the ion concentration (Nernst voltage). This potential difference acts as a shift in the threshold voltage.

Figure 5:
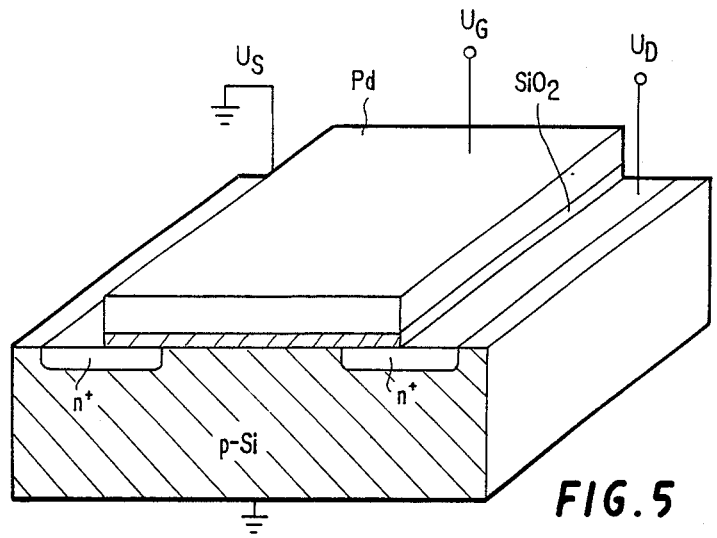

The most well-known example of a sensor for measuring in gases is the MOSFET with palladium gate metal shown diagrammatically in FIG. 5 which makes it possible to detect hydrogen or hydrogen-containing gases. In this case the hydrogen molecules from the gas accumulate at the palladium surface and dissociate into atomic hydrogen. The latter migrates through the palladium layer and builds up, at the palladium/$SiO_2$ phase boundary, a dipole layer which alters the work function of the palladium gate electrode and consequently the threshold voltage.

The object of the invention is to provide sensors for selectively determining liquid-phase or gas-phase components, which sensors are not restricted to detecting a single species to be analyzed but, as a result of slight modification, make possible the specific detection of a multiplicity of species to be analyzed, as a result of which not only is easy adaptation to various problems achieved, but also a simplification of manufacturing technique.

It has now been found that the chemical substance group comprising the heteropolysiloxanes enters into an interaction with species to be analyzed (e.g. gas molecules, dissolved ionic species etc.) which measurably changes the electrical properties of the heteropolysiloxane (for example, dielectric constant, specific conductance etc.). If the heteropolysiloxanes are used in electrical sensors (for example, field effect transistors or capacitors), it is consequently possible to obtain information about the presence or concentration of certain species to be analyzed from the change in the electrical properties of the heteropolysiloxane. As a result of suitable functionalization of the heteropolysiloxane (for example incorporation of functional groups) it is possible to establish the required specificity and selectivity for the analytical species to be determined.

Accordingly, the present invention relates, according to an embodiment, to a sensor for selectively determining liquid-phase or gas-phase components in the form of a field effect transistor, comprising a semiconductor substrate; at the surface of the semiconductor substrate at least two drain and source regions with a dopant type opposite to that of the semiconductor substrate separated by a channel; drain and source electrodes which are in electrically conducting contact with said drain and source regions; a gate insulator layer on the channel; a sensitive layer consisting of a heteropolydiloxane on the gate insulator layer, it being possible for the sensitive layer to come into contact with the components to be determined; and a gate or reference electrode.

According to another embodiment, the invention relates to a capacitive sensor for selectively determining liquid-phase or gas-phase components, comprising two or more electrodes and one or more dielectrics between said electrodes, at least one dielectric consisting of a heteropolysiloxane and being capable of coming into contact with the components to be determined.

According to a further embodiment, the invention relates to an arrangement for simultaneously determining several liquid-phase or gas-phase components, comprising several sensors or the type mentioned above with different, selective sensitivity for the components to be determined in each case.

Figure 2A:
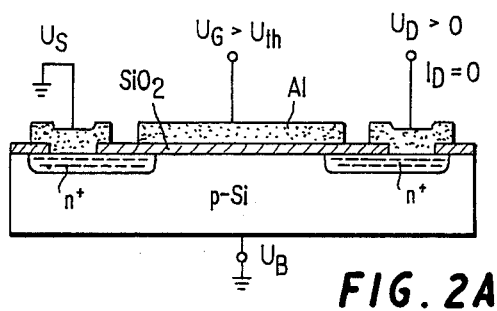
Figure 2B:
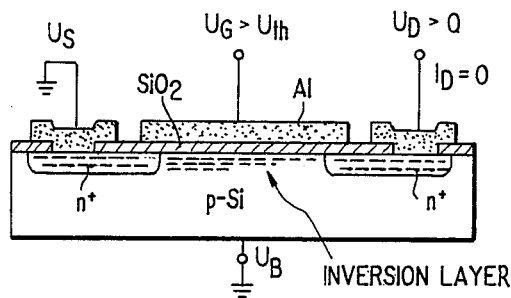
Figure 3A:
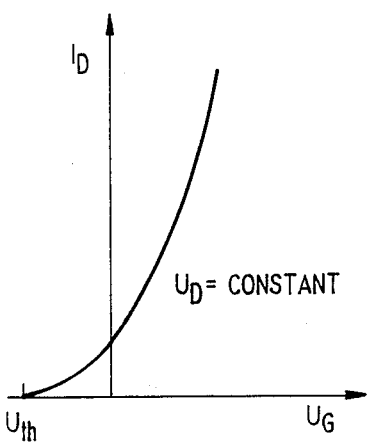
Figure 3B:
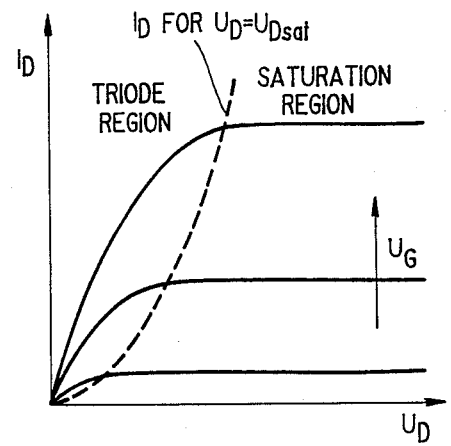
Figure 4:
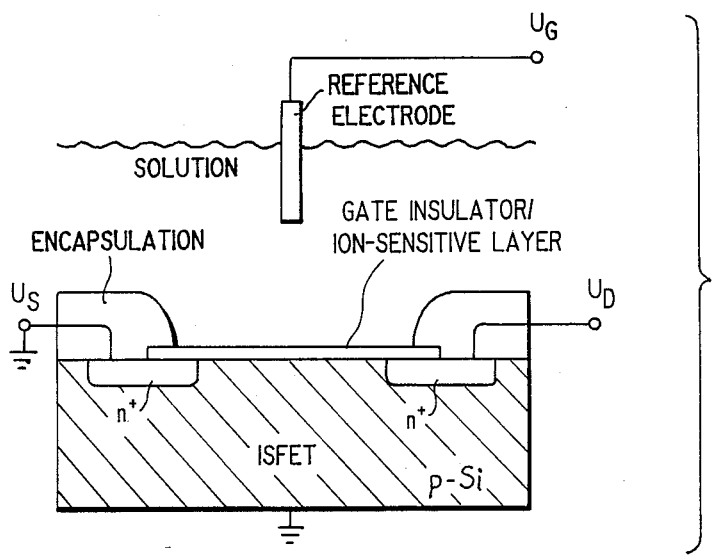
Figure 6A:
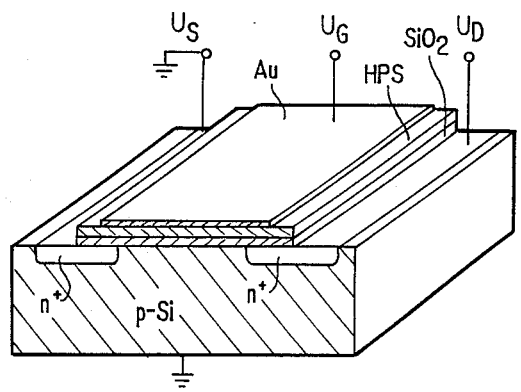
Figure 6B:
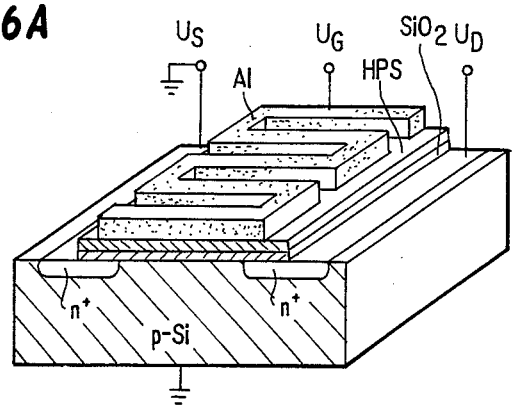
Figure 7A:
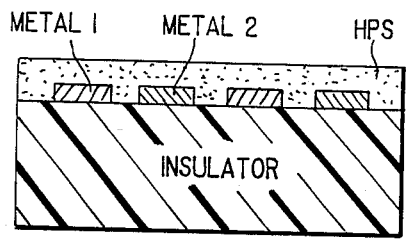
Figure 7B:
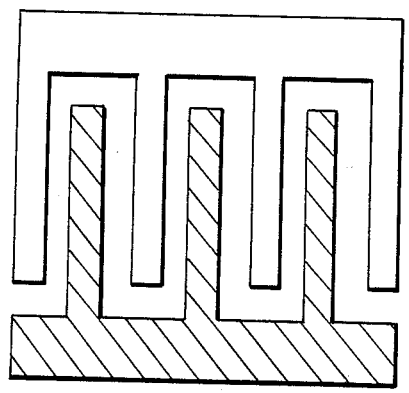
Figure 7C:
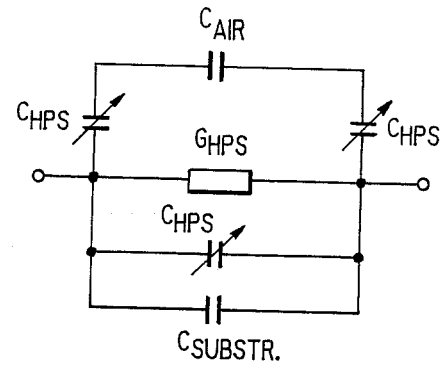
Figure 8:
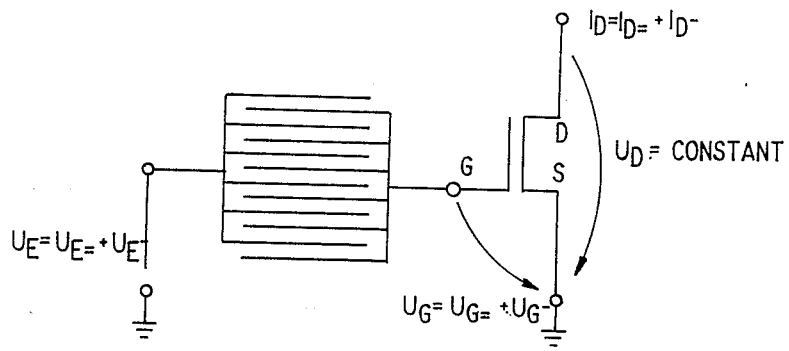
Figure 9A:
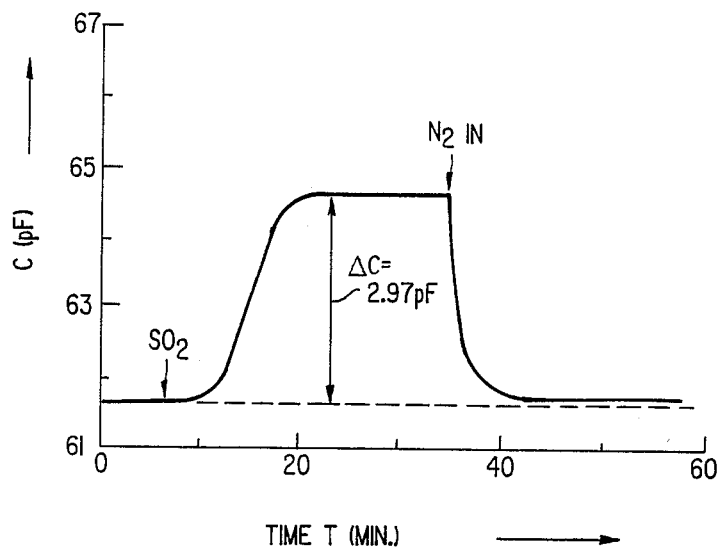
Figure 9B:
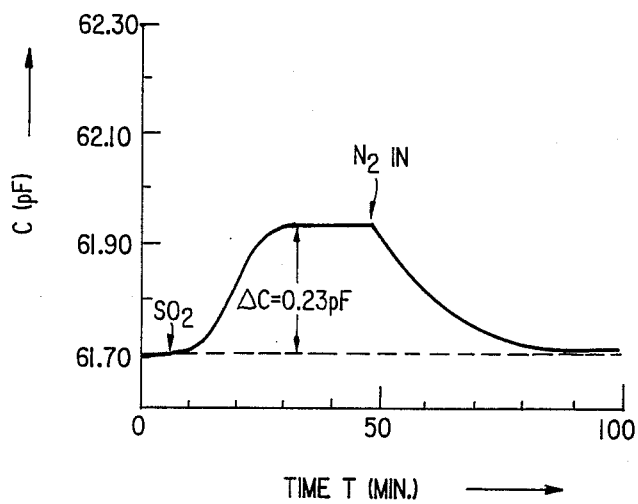
Figure 10:
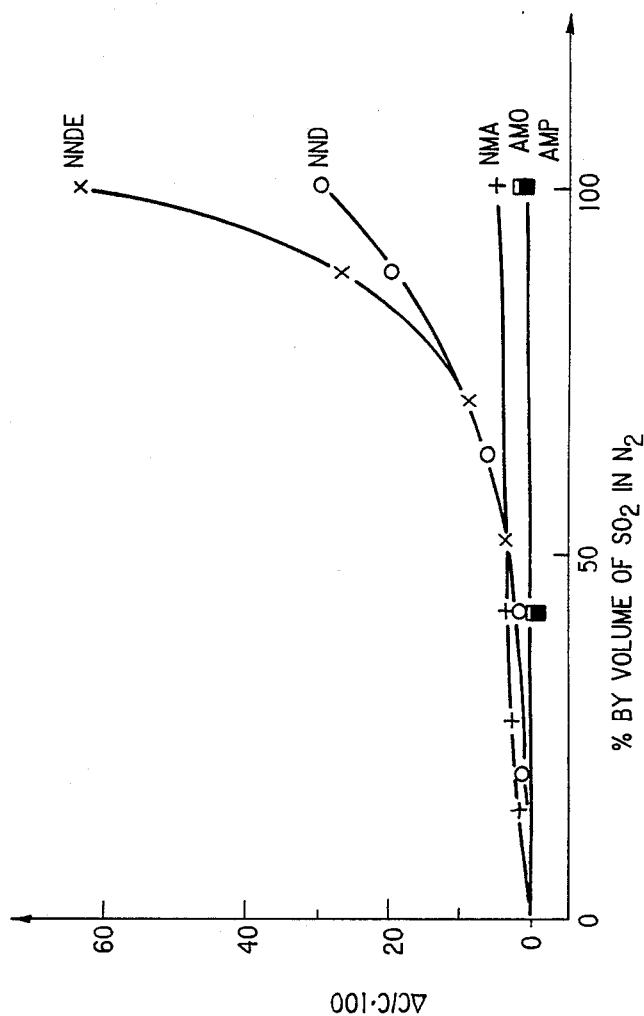
Figure 11:
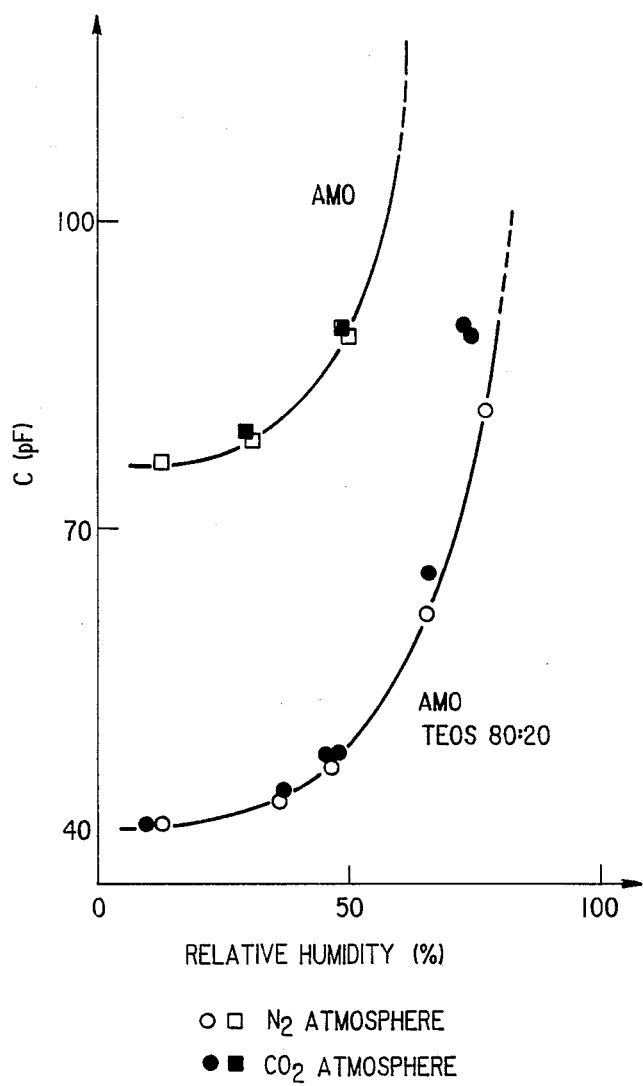
Figure 12:
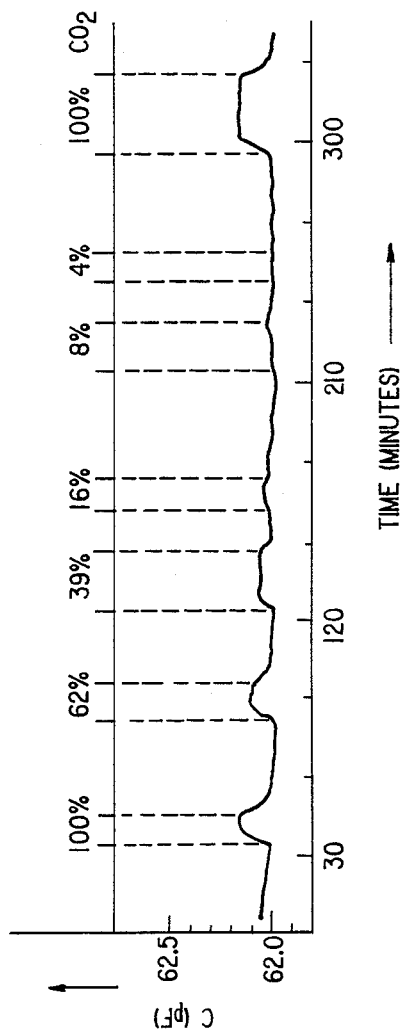
Figure 13:
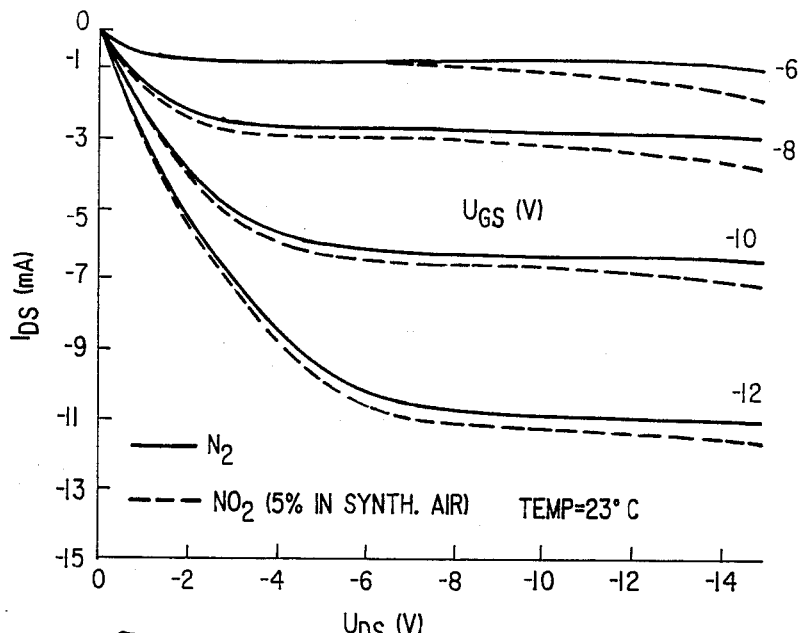
Figure 14:
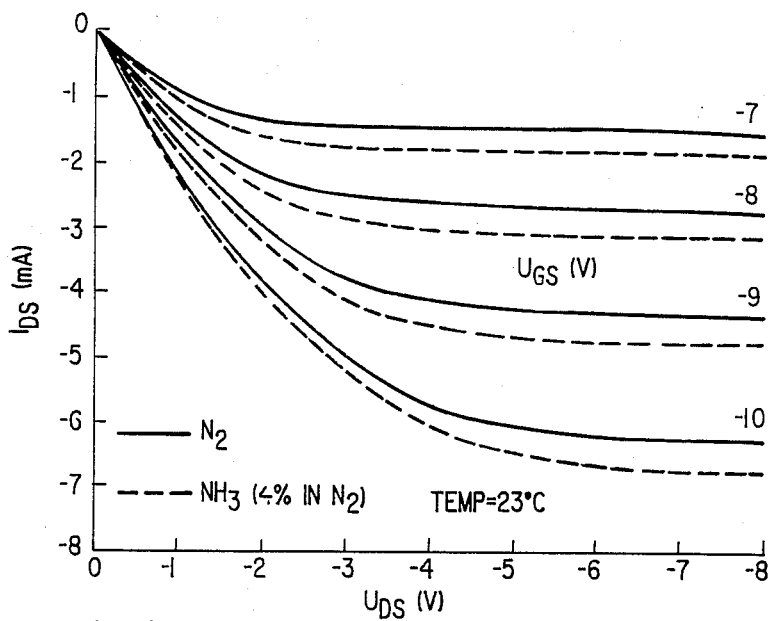

The invention is explained below in more detail on the basis of preferred embodiments with reference to the drawings. The drawings show:

FIG. 1: a diagrammatic representation of a conventional field effect transistor;

FIGS. 2A and 2B: two operating states of the field effect transistor of FIG. 1, namely (a) blocking and (b) conducting;

FIGS. 3A and 3B: the characteristic input and output curves of an n-channel field effect transistor;

FIG. 4: a diagrammatic cross-section through an ion-sensitive field effect transistor for measuring in liquids;

FIG. 5 a diagrammatic cross-section through a field effect transistor with palladium gate metal for measuring in hydrogen-containing gases;

FIG. 6a: an embodiment of a field effect transistor according to the invention with a heteropolysiloxane layer and a gate metal layer consisting of thin gold (100 Å);

FIG. 6b: another embodiment of a field effect transistor according to the invention with a heteropolysiloxane layer and a gate metal layer consisting of aluminum in meander form;

FIG. 7a: a diagrammatic cross-section through an embodiment of a capacitive sensor according to the invention;

FIG. 7b: a diagrammatic planview of the capacitive sensor of FIG. 7a;

FIG. 7c: the electrical equivalent circuit diagram of the capacitive sensor of FIG. 7a;

FIG. 8: a circuit diagram for the coupling of a capacitive sensor to a field effect transistor;

FIG. 9a and FIG. 9b: the variation of the capacitance of a sensor according to FIG. 7 with time on altering the composition of the gas atmosphere;

FIG. 10: the relative change in capacitance of sensors according to FIG. 7, which are coated with various heteropolysiloxanes containing amino groups, as a function of the $SO_2$ content of the atmosphere;

FIG. 11: the dependence of the capacitance of two sensors according to FIG. 7 on the relative humidity at 20° C. in an $N_2$ atmosphere or $CO_2$ atmosphere;

FIG. 12: the measurement record of a sensor according to FIG. 7 with a heteropolysiloxane layer containing $CuCl_2$ in the determination of $CO_2$;

FIG. 13: the family of characteristic output curves of a field effect transistor according to the invention, which has a gate metal layer consisting of aluminum in meander form and which is coated with an HPS layer containing $CuCl_2$, in $NO_2$/synthetic air and in $N_2$; and FIG. 14: the family of characteristic output curves of a field effect transistor according to the invention, which has a gate metal layer consisting of aluminum in meander form and which is coated with a $CuCl_2$-containing HPS layer, in $NH_3/N_2$ and in $N_2$.

The sensors according to the invention can be used to detect any species to be analyzed in a liquid or gaseous phase. For simplicity, reference is made only to gas sensors in the following description, but the invention is not restricted to these embodiments but can be used with suitable modifications, which present no difficulties for those skilled in the art, for example, for detecting neutral or ionic species to be analyzed in liquid media. For example, the ISFET shown in FIG. 4, which has an HPS layer, according to the invention, as ion-selective layer, is suitable for this purpose.

The field effect transistor (hereinafter: FET) according to the invention shown diagrammatically in FIG. 6 has n+-doped drain or source regions, which define a channel between them, on a semiconductor substrate (for example, p-Si). Above the channel there is a gate insulator layer having a thickness, for example, 20 to 1,000 nm, preferably 30 to 200 nm. The gate insulator layer may be single-layer or multi-layer and consists preferably of $SiO_2$ or $Si_3N_4$.

The sensitive layer consisting of a heteropolysiloxane (hereinafter: HPS) is applied to the gate insulator layer. This sensitive layer has a thickness of, for example, 10 to 1,000 nm, preferably 100 to 500 nm.

In the embodiment of an FET according to the invention shown in FIG. 6, a gate electrode is provided above the HPS layer. In gas sensors such a gate electrode has proved necessary in order to obtain a defined gate potential, which is a precondition for stable and reproducible results. However, the gate electrode in the embodiment shown must be permeable to the analytical species to be determined (for example, the gas). This is achieved in the embodiment shown in FIG. 6a by a very thin gold layer (for example, 5 to 20 nm). FIG. 6b shows an alternative method of solution, namely the use of a fairly thick gate electrode (for example, of aluminum) which makes penetration of the gas to be determined possible as a result of its physical form (for example, perforations or meander-like structure).

The operation of the FET gas sensor according to the invention is based on the fact that, in the adsorbed state, gas molecules exert an electrical action due to dipole moments. The critical factor is not the dipole moment of the free gas molecule, but how the dipole moment of a molecule of the sensor layer changes when a gas molecule is deposited up. In this connection, a distinction must be made between whether the gas can penetrate the HPS layer or not, i.e. whether a compact or porous HPS layer is present. In the case of compact HPS layers, the deposition of dipoles on the layer may result in a change in $Q_{is}$, i.e. the parameter which represents the effective charge in the gate insulator. In the case of a porous HPS layer, the gas molecules are able to penetrate the pores of the layer so that, additionally, the dielectric constant, which is dependent, inter alia, on the number of dipoles present, is changed. A further possibility is a change in the electrical conductance of the HPS layer on the gate due to interaction with the species to be analyzed. This change in conductance may be utilized by means of two, instead of only one, gate electrodes or by means of an alternating voltage instead of a direct voltage on the gate.

If an FET with gate electrode is used, the change in the work function of the gate metal due to the dipoles deposited may also be added to the described electrical effects in the HPS layer as an additional influencing parameter. The said influencing parameters effect a change in the threshold voltage, and consequently in the drain current, for constant drain-source voltage, so that it is possible to determine the gas quantitatively with short response times.

The change in the dielectric constant due to the adsorption of gas molecules may also be measured with the capacitive sensors according to the invention, which have an HPS dielectric. For these capacitive sensors constructional configurations of any desired type are conceivable. For example, a plate capacitor with the following layer construction may be used: silicon/silicon dioxide/HP/metal (MIS structure). To facilitate the access of the gas being measured to the HPS layer, an air gap may be provided between the metal and the HPS layer. However, this is less preferred and is unnecessary if a metal layer which is permeable to gas is used.

FIG. 7 shows a preferred embodiment of a capacitive sensor according to the invention. In order to achieve a planar structure, the electrodes are of interdigitate structure. This comprises, for example, aluminum electrode pairs vapor-deposited on a ceramic substrate, each electrode consisting, for example, of 60 fingers with a height of 1 μm and a width of 20 μm with a finger-spacing of 20 μm. On and between the finger-like electrodes there is a thin HPS layer as dielectric.

FIG. 7c shows the electrical equivalent circuit of this capacitor structure. It consists of a conductance element which comes about as a result of the nonideal insulator properties of the HPS layer, of the two stray capacitances $C_{air}$ and $C_{substrate}$, and also of the series or parallel circuit consisting of 3 capacitances, with the HPS layer as dielectric, whose value may change under the gas atmosphere.

The capacitance change resulting from the adsorption of gas molecules may be measured, for example, by connecting the capacitor in an oscillatory circuit in which the change in capacitance produces a change in the frequency of an oscillator.

Another possibility is the coupling of the capacitor to a conventional FET as shown in FIG. 8. For this purpose one electrode of the capacitor is connected to the gate electrode of the FET in an electrically conducting manner. The second electrode of the capacitor has a direct voltage applied to it on which an alternating voltage is superimposed. With constant drain-source voltage, the gas concentration can then be determined from the change in amplitude and phase of the alternating current component of the drain current.

To determine several components simultaneously, it is possible according to the invention to use measuring arrangements which involve two or more FET sensors and/or capacitive sensors each having different sensitivity for the various components to be determined. For example, gas sensors and humidity sensors may be arranged on a single chip. This measuring arrangement makes it possible to compensate for the effect of humidity on the changes in the electrical properties of the sensor layer produced by the gas molecules. Simultaneous use of several sensors also makes it possible to perform, for example, a total determination of several components in addition to one or more individual determinations, the concentration of the other components being obtained from a difference calculation.

The heteropolysiloxanes (HPS) used, according to the invention, as sensor layers are organically modified silicates. In this connection, the modification is performed primarily by incorporating suitable functional groups and by reaction with other metal compounds which can also be hydrolyzed and condensed. This modification produces surface sites (adsorption centers) which make the desired selective interaction possible with the species to be analyzed (for example, gas molecules).

Thus, HPS layers with primary amino groups, for example, respond clearly in their electrical characteristics to $H_2O$, $HCl$ and $NH_3$ and slightly to $SO_2$ and $CO_2$ (especially in a moist atmosphere). HPS layers with tertiary amino groups exhibit a rise in capacitance which is dependent on the $SO_2$ content of the gas atmosphere, and the capacitance of cyanopropyl-HPS layers containing $CuCl_2$ increases as a function of the $CO_2$ partial pressure.

FIG. 9 shows the variation with time of the capacitance of an interdigitate structure according to FIG. 7, which has a condensate of N,N-dimethyl-3-aminopropyltrimethoxysilane (NND) as dielectric, as the $SO_2$ content of the gas atmosphere changes.

Similarly, FIG. 10 shows the relative change in capacitance of the interdigitate structure according to FIG. 7 as a function of the $SO_2$ content of the atmosphere (20° C.). In this case condensates of various HPSs, containing amino groups, namely of 3-aminopropyltriethoxysilane (AMO), aminophenyltrimethoxysilane (AMP), N-methyl-3-aminopropyltrimethoxysilane (NMA), N,N-dimethyl-3-aminopropyltrimethoxysilane (NND) and N,N-diethyl-3-aminopropyltrimethoxysilane (NNDE), are used as dielectrics. In this case it emerges that the influence of $SO_2$ is most marked for the HPSs with tertiary amino groups (NMD and NMDE).

The relative change in capacitance $\Delta C/C$ is calculated from the following formula:

$$\Delta C/C = \frac{C(SO_2) - C(N_2)}{C(N_2)}$$

$C(N_2)$: capacitance in pure nitrogen, $C(SO_2)$: capacitance in nitrogen, containing $SO_2$.

FIG. 11 shows the capacitance of two interdigitate structures according to FIG. 7 as a function of the relative humidity at 20° C. in an $N_2$ atmosphere and $CO_2$ atmosphere respectively. The dielectrics used are a condensate of AMO or a mixed condensate of AMO and tetraethoxysilane (TEOS). For both HPS dielectrics, the capacitance of the interdigitate structure is clearly dependent on the $H_2O$ partial pressure, the pure AMO condensate, because of its higher proportion of polar $NH_2$ groups, responding more sensitively to the changes in the $H_2O$ partial pressure.

FIG. 12 shows the measurement record of an interdigitate structure according to FIG. 7 having the $CuCl_2$-containing coating from Example 4 for the determination of $CO_2$ (21° C.). The percentages specified denote the proportion of $CO_2$ by volume in the gas atmosphere. In the time intervals which are not described in more detail, pure nitrogen flows through the apparatus.

FIG. 13 shows the output family of characteristic curves of an FET with a gate metal layer of aluminum in meander form and coated with an HPS layer containing $CuCl_2$ which were measured in an atmosphere of 5% $NO_2$ in synthetic air and in $N_2$ respectively. The absolute value of the drain current increases when $NO_2$ is applied to the sensor. The curves were measured on a p-channel transistor.

FIG. 14 shows the output family of characteristic curves of an FET having a gate metal layer of aluminum in meander form and coated with an HPS layer containing $CuCl_2$ which were measured in an atmosphere of 4% $NH_3$ in $N_2$ and in $N_2$ respectively. The effect of the gas to be detected, namely $NH_3$, is revealed in an increase in the absolute value of the drain current of the p-channel FET.

A group of heteropolysiloxanes especially preferred for the sensors according to the invention are obtained by hydrolysis and polyycondensation of (a) at least one organofunctional silane of the general formula I

$$SiR'_bX_c(R''Y)_{(4-b-c)} \qquad (I)$$

in which R' denotes alkyl, alkenyl, aryl, aralkyl or alkylaryl, X represents hydrogen, halogen, alkoxy, acyloxy or $-NR_2$ (R=hydrogen and/or alkyl), R" represents straight-chain or branched alkylene, which may be interrupted by oxygen of sulfur atoms or $-NH-$ groups, phenylene, alkylphenylene or alkylenephenylene, Y denotes halogen or an optionally alkyl-substituted amino, optionally alkyl-substituted anilino, aldehyde, alkylcarbonyl, arylcarbonyl, carboxyl, hydroxyl, mercapto, cyano, hydroxyphenyl, diazo, carboxylic acid alkyl ester, sulfonic acid ($SO_3H$), phosphoric acid ($PO_3H_2$), phosphino, dialkylphosphino, diarylphosphino, alkylarylphosphino, imidazolino, 4,5-dihydroimidazolino, pyridino, or epoxy group, b has the value 0, 1 or 2, c has the value 1, 2 or 3 and (b+c) have the value 1, 2 or 3;

(b) optionally at least one silicon-functional silane of the general formula II $$SiX_4 \quad (II)$$

in which X has the above meaning, but not all the X radicals are hydrogen;

(c) optionally at least one organosilane of the general formula III $$SiR'_a X_{(4-a)} \quad (III)$$

in which X and R' have the above meaning and a has the value 1, 2 or 3;

(d) optionally at least one low-volatility oxide which is soluble in the reaction medium or at least one compound of an element of the main groups Ia to Va or the subgroups IVb or Vb of the periodic system which is soluble in the reaction medium and which forms a low-volatility oxide; and (e) optionally at least one metal compound, soluble in the reaction medium, which catalyzes a reaction of the species to be analyzed, and/or an organic compound, soluble in the reaction medium, which enters into a chemical reaction with the species to be analyzed; optionally in the presence of a condensation catalyst and/or of an organic solvent.

The heteropolysiloxane prepared in this manner preferable contains, relative to the oxide units, 20 to 100 percent by weight of component (a) and in each case 0 to 80 percent by weight of the components (b), (c), (d) and/or e).

These and similar heteropolysiloxanes, and also methods for preparing them, are described, for example, in German Offenlegungsschrifts 2,758,415 and 2,925,969.

As regards the preferred product compositions and special examples of the components (a) to (d), reference is made to these patent publications.

Metal compounds soluble in the reaction medium, for example, compounds of elements of the main groups IIIa and IVa, and also of the subgroups IVb up to and including VIIIb and Ib of the periodic system, which catalyze a reaction of the analytical species to be determined and which can optionally be reduced to the metal, are suitable as components (e). For example, metals of the platinum group and compounds or complex compounds of said metals, for example $PtCl_2$, $Pd(NO_3)_2$, $Rh(NO_3)_3$ and the so-called Vaska compound $((C_6H_5)_3P)_2IrCl(CO))$, are especially preferred for determining the gases $O_2$, $NO_x$, CO and also various hydrocarbons.

For components (e), use may also be made of organic compounds, soluble in the reaction medium, which can enter into an interaction with the species to be analyzed, for example a Brönstedt acid base interaction, an electron donor-acceptor interaction or a chemical reaction, for example a Redox reaction. An organic compound suitable for the last-named type of reaction is, for example, hydroquinone of oxygen is being detected.

The method used to prepare the HPS is described as the sol-gel process. Starting from liquid or soluble initial compounds, molecules and molecular aggregates with increasing molecular weight are obtained by progressive condensation. This leads to a colloidal disperse solution (sol) which thickens to an amorphous solid (gel) as the primary reaction product as a result of further condensation. This may optionally then be post-treated further.

The water required stoichiometrically for the hydrolysis is either added at least in part to the polycondensation system or else drawn completely from the air humidity.

Sensitive HPS layers can be prepared in various manners. For example, it is possible to start from the dissolved state of the starting compounds so that the entire sol-gel process then proceeds in the layer. Coatings can also be performed in the sol state. Finally, in the case of soluble gels, it is also possible to dissolve the product in an organic solvent which is then applied as a solution.

Special examples of the coating substances for preparing sensitive HPS layers are specified below.

Example 1 ($NH_3$- and $H_2O$-sensitive layers)

2 ml of 3-aminopropyltriethoxysilane are dissolved in 6 ml of n-butanol along with 0.23 ml of water and stirred for 2 hours at room temperature. The reaction mixture obtained may be used as the coating substance for $NH_3$- and $H_2O$-sensitive layers.

Example 2 ($CO_2$-sensitive layers)

2.5 ml of 3-aminopropyltriethoxysilane and 0.6 ml of tetraethoxysilane are dissolved in 9.3 ml of n-butanol and stirred for 2 hours at room temperature. The reaction mixture obtained may be used as the coating substance for $CO_2$-sensitive layers.

Example 3 ($SO_2$-sensitive layers)

2.0 ml of N,N-dimethyl-3-aminopropyltrimethoxysilane or 2 ml of N,N-diethyl-3-aminopropyltrimethoxysilane are dissolved with 0.25 ml of water in 6 ml of n-butanol and stirred for 2 hours at room temperature. The reaction mixture obtained may be used as the coating substance for $SO_2$-sensitive layers.

Example 4 ($CO_2$-sensitive layers)

11.4 ml of 3-cyanopropyltrimethoxysilane are dissolved in 34.2 ml of n-butanol along with 1.7 ml of 1M hydrochloric acid. 319 mg of copper(II) chloride are added to this solution and dissolved. The reaction mixture is stirred for 2 hours at room temperature and can then be used as the coating substance for $CO_2$-sensitive layers.

The application of the coating substances is preferably performed by the so-called spin-on technique (spinning down), it being possible to vary the layer thickness by means of the rotary speed. In general, the layer thicknesses aimed at are obtained with a rotary speed of about 1,000 to 2,000 rev/min; however, rotary speeds of up to 10,000 rev/min may also be used.

Example 5 (preparation of an HPS-coated FET)

A coating substance as prepared in one of the Examples 1 to 4 is applied to the gate insulator layer of an FET, either as such or after optional separation from the organic solvent, and hardened. For example, the coated substrate may be stored protected from dust for 6 hours at room temperature and then hardened for 16 hours at elevated temperature, for example 120° C.

The HPS layer obtained is then patterned in the usual manner, preferably by wet-chemical etching using the photoresist method.

The gate metal is deposited on the patterned HPS layer, for example by sputtering on a thin layer of gold.

Example 6 (preparation of an HPS-coated FET)

A coating substance as prepared in one of the Examples 1 to 4 is applied to the gate insulator layer of an FET with an Al gate electrode in meander form and spun-down in a lacquer spinner. The sensor is then hardened for 3 hours at room temperature and 16 hours at 120° C.

Example 7 (preparation of a capacitive sensor)

A drop of a coating substance according to one of the Examples 1 to 4 is applied to the interdigitate structure according to FIG. 7 and spun down in a lacquer spinner at 2,000 rev/min. The capacitor structures with the thin HPS layer on or between the finger-like electrodes are then hardened for 16 hours in an annealing furnace at 120° C.

We claim:

1. Sensor for selectively determining liquid-phase or gas-phase components in the form of a field effect transistor, comprising a semiconductor substrate; at the surface of the semiconductor substrate at least two drain and source regions with a dopant type opposite the semiconductor substrate and separated by a channel; drain and source electrodes which are in electrically conducting contact with said drain and source regions; a gate insulator layer on the channel; a sensitive layer consisting of a heteropolysiloxane on the gate insulating layer, it being possible for the sensitive layer to come into contact with the components to be determined; and a gate or reference electrode.

2. Sensor as claimed in claim 1, wherein the gate insulator layer has a thickness of 30 to 200 nm.

3. Sensor as claimed in claim 1, wherein the sensitive layer has a thickness of 10 to 1,000 nm.

4. Sensor as claimed in claim 1, wherein the sensitive layer consists of a heteropolysiloxane which has been prepared by hydrolysis and condensation of at least one organofunctional silane of the general formula I $$SiR'_bX_c(R''Y)_{(4-b-c)} \qquad (I)$$

in which R' denotes alkyl, alkenyl, aryl, aralkyl or alkylaryl, X represents hydrogen, halogen, alkoxy, acyloxy or —NR2 (R=hydrogen and/or alkyl), R" represents straight-chain or branched alkylene, which may be interrupted by oxygen or sulfur atoms or —NH— groups, phenylene, alkylphenylene or alkylenephenylene, Y denotes halogen or an alkyl-substituted amino, alkyl-substituted anilino, aldehyde, alkylcarbonyl, arylcarbonyl, carboxyl, hydroxyl, mercapto, cyano, hydroxyphenyl, diazo, carboxylic acid alkyl ester, sulfonic acid (SO3H), phosphoric acid (PO3H2), phosphino, dialkylphosphino, diarylphosphino, alkylarylphosphino, imidazolino, 4,5-dihydroimidazolino, pyridino or epoxy group, b has the value 0, 1 or 2, c has the value 1, 2 or 3 and (b+c) have the value 1, 2 or 3.

5. Sensor according to claim 4, wherein said heteropolysiloxane prepared by hydrolysis and condensation is prepared in the presence of a condensation catalyst.

6. Sensor according to claim 4, wherein said heteropolysiloxane prepared by hydrolysis and condensation is prepared in the presence of an organic solvent.

7. Sensor according to claim 4, wherein said heteropolysiloxane prepared by hydrolysis and condensation is prepared in the presence of a condensation catalyst and an organic solvent.

8. Sensor as claimed in claim 1, wherein the gate electrode is permeable to the components to be determined.

9. Sensor as claimed in claim 1, wherein the sensitive layer consists of a heteropolysiloxane which has been prepared by hydrolysis and condensation of (a) at least one organofunctional silane of the general formula I $$SiR'_bX_c(R''Y)_{(4-b-c)} \qquad (I)$$

in which R' denotes alkyl, alkenyl, aryl, aralkyl or alkylaryl, X represents hydrogen, halogen, alkoxy, acyloxy or —NR2 (R=hydrogen and/or alkyl), R" represents straight-chain or branched alkylene, which may be interrupted by oxygen or sulfur atoms or —NH— groups, phenylene, alkylphenylene or alkylenephenylene, Y denotes halogen or an alkyl-substituted amino, alkyl-substituted anilino, aldehyde, alkylcarbonyl, arylcarbonyl, carboxyl, hydroxyl, mercapto, cyano, hydroxyphenyl, diazo, carboxylic acid alkyl ester, sulfonic acid (SO3H), phosphoric acid (PO3H2), phosphino, dialkylphosphino, diarylphosphino, alkylarylphosphino, imidazolino, 4,5-dihydroimidazolino, pyridino or epoxy group, b has the value 0, 1 or 2, c has the value 1, 2 or 3 and (b+c) have the value 1, 2 or 3; and at least one compound selected from the group consisting of:

(b) at least one silicon-functional silane of the general formula II $$SiX_4 \qquad (II)$$

in which X has the above meaning, but not all the X radicals are hydrogen;

(c) at least one organosilane of the general formula III $$SiR'_aX_{(4-a)} \qquad (III)$$

in which X and R' have the above meaning and a has the value 1, 2 or 3;

(d) at least one low-volatility oxide soluble in the reaction medium or at least one compound of an element of the main groups Ia to Va or the subgroups IVb or Vb of the periodic system which is soluble in the reaction medium and forms a low-volatility oxide; and (e) at least one metal compound, soluble in the reaction medium, which catalyzes a reaction of the species to be analyzed, and/or one organic compound, soluble in the reaction medium, which enters into a chemical reaction with the species to be analyzed.

10. Sensor according to claim 9, wherein said heteropolysiloxane prepared by hydrolysis and condensation is prepared in the presence of a condensation catalyst.

11. Sensor according to claim 9, wherein said heteropolysiloxane prepared by hydrolysis and condensation is prepared in the presence of an organic solvent.

12. Sensor according to claim 9, wherein said heteropolysiloxane prepared by hydrolysis and condensation is prepared in the presence of a condensation catalyst and an organic solvent.

13. Sensor for selectively determining liquid-phase or gas-phase components, comprising two or more electrodes and one or more dielectrics between said electrodes, at least one dielectric consisting of a heteropolysiloxane and being capable of coming into contact with the components to be determined.

14. Sensor as claimed in claim 13, wherein the electrodes have an interdigitate structure.

15. Sensor as claimed in claim 13, wherein an electrode of the sensor is connected in an electrically conducting manner with the gate electrode of a field effect transistor.

16. Sensor as claimed in claim 13, wherein the dielectric consists of a heteropolysiloxane which has been prepared by hydrolysis and condensation of at least one organofunctional silane of the general formula I

  (1)

in which R' denotes alkyl, alkenyl, aryl, aralkyl and alkylaryl, X represents hydrogen, halogen, alkoxy, acyloxy or —NR$_2$ (R=hydrogen and/or alkyl), R" represents straight-chain or branched alkylene, which may be interrupted by oxygen or sulfur atoms or —NH— groups, phenylene, alkylphenylene or alkylenephenylene, Y denotes halogen or an alkyl-substituted amino, alkyl-substituted anilino, aldehyde, alkylcarbonyl, arylcarbonyl, carboxyl, hydroxyl, mercapto, cyano, hydroxyphenyl, diazo, carboxylic acid alkyl ester, sulfonic acid (SO$_3$H), phosphoric acid (PO$_3$H$_2$), phosphino, dialkylphosphino, diarylphosphino, alkylarylphosphino, imidazolino, 4,5-dihydroimidazolino, pyridino or epoxy group, b has the value 0, 1 or 2, c has the value 1, 2 or 3 and (b+c) have the value 1, 2 or 3.

17. Sensor according to claim 16, wherein said heteropolysiloxane prepared by hydrolysis and condensation is prepared in the presence of a condensation catalyst.

18. Sensor according to claim 16, wherein said heteropolysiloxane prepared by hydrolysis and condensation is prepared in the presence of an organic solvent.

19. Sensor according to claim 16, wherein said heteropolysiloxane prepared by hydrolysis and condensation is prepared in the presence of a condensation catalyst and an organic solvent.

20. Sensor as claimed in claim 13, wherein the dielectric consists of a heteropolysiloxane which has been prepared by hydrolysis and condensation of
    (a) at least one organofunctional silane of the general formula I

  (1)

in which R' denotes alkyl, alkenyl, aryl, aralkyl or alkylaryl, X represents hydrogen, halogen, alkoxy, acyloxy or —NR$_2$ (R=hydrogen and/or alkyl), R" represents straight-chain or branched alkylene, which may be interrupted by oxygen or sulfur atoms or —NH— groups, phenylene, alkylphenylene or alkylenephenylene, Y denotes halogen or an alkyl-substituted amino, alkyl-substituted anilino, aldehyde, alkylcarbonyl, arylcarbonyl, carboxyl, hydroxyl, mercapto, cyano, hydroxyphenyl, diazo, carboxylic acid alkyl ester, sulfonic acid (SO$_3$H), phosphoric acid (PO$_3$H$_2$), phosphino, dialkylphosphino, diarylphosphino, alkylarylphosphino, imidazolino, 4,5-dihydroimidazolino, pyridino or epoxy group, b has the value 0, 1 or 2, c has the value 1, 2 or 3 and (b+c) have the value 1, 2 or 3; and
at least one compound selected from the group consisting of:

(b) at least one silicon-functional silane of the general formula II

  (II)

in which X has the above meaning, but not all the X radicals are hydrogen;

(c) at least one organosilane of the general formula III

  (III)

in which X and R' have the above meaning and a has the value 1, 2 or 3;

(d) at least one low-volatility oxide soluble in the reaction medium or at least one compound of an element of the main groups Ia to Va or of the subgroups IVb or Vb of the periodic system which is soluble in the reaction medium and forms a low-volatility oxide; and (e) at least one metal compound, soluble in the reaction medium, which catalyzes a reaction of the species to be analyzed, and/or organic compound, soluble in the reaction medium, which enters into a chemical reaction with the species to be analyzed.

21. Sensor according to claim 20, wherein said heteropolysiloxane prepared by hydrolysis and condensation is prepared in the presence of a condensation catalyst.

22. Sensor according to claim 20, wherein said heteropolysiloxane prepared by hydrolysis and condensation is prepared in the presence of an organic solvent.

23. Sensor according to claim 20, wherein said heteropolysiloxane prepared by hydrolysis and condensation is prepared in the presence of a condensation catalyst and an organic solvent.

24. Arrangement for simultaneously determining several liquid-phase or gas-phase components, comprising several sensors for selectively determining liquid-phase or gas-phase components with different selective sensitivity for the components to be determined in each case, each sensor being in the form of a field effect transistor, comprising a semiconductor substrate, at the surface of the semiconductor substrate at least two drain and source regions with a dopant type opposite the semiconductor substrate and separated by a channel, drain and source electrodes which are in electrically conducting contact with said drain and source regions, a gate insulating layer, a sensitive layer comprising a heteropolysiloxane on the gate insulating layer it being possible for the sensitive layer to come into contact with the components to be determined, and a gate or reference electrode.

25. Arrangement for simultaneously determining several liquid-phase or gas-phase components, comprising several sensors for selectively determining liquid-phase or gas-phase components with different selective sensitivity for the components to be determined in each case, each sensor comprising two or more electrodes and one or more dielectrics between said electrodes, at least one dielectric consisting of a heteropolysiloxane and being capable of coming into contact with the components to be determined.

26. Arrangement as claimed in claim 25 with different selective sensitivity for the components to be determined in each case, wherein an electrode of each sensor is connected in an electrically conducting manner with the gate electrode of a field effect transistor.

* * * * *